(12) United States Patent
Kirkpatrick

(10) Patent No.: US 10,098,332 B2
(45) Date of Patent: Oct. 16, 2018

(54) METHODS AND COMPOSITIONS FOR DETERMINING BOVINE OVULATION RATE

(71) Applicant: Wisconsin Alumni Research Foundation, Madison, WI (US)

(72) Inventor: Brian Wayne Kirkpatrick, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 399 days.

(21) Appl. No.: 14/321,036

(22) Filed: Jul. 1, 2014

(65) Prior Publication Data

US 2015/0007358 A1 Jan. 1, 2015

Related U.S. Application Data

(60) Provisional application No. 61/841,723, filed on Jul. 1, 2013.

(51) Int. Cl.
*A01K 67/02* (2006.01)
*C12Q 1/6883* (2018.01)

(52) U.S. Cl.
CPC ............ *A01K 67/02* (2013.01); *C12Q 1/6883* (2013.01); *C12Q 2600/124* (2013.01); *C12Q 2600/156* (2013.01)

(58) Field of Classification Search
CPC ...................................................... A01K 67/02
See application file for complete search history.

(56) References Cited

PUBLICATIONS

Morris et al. (2010, Livestock Science, vol. 128, pp. 193-196).*
Khatkar et al. (2007, Genetics, vol. 176, pp. 763-772).*

* cited by examiner

*Primary Examiner* — Thaian N Ton
(74) *Attorney, Agent, or Firm* — Boyle Fredrickson S.C.

(57) ABSTRACT

Described herein are methods and compositions for modulating bovine birth rate by following a breeding scheme based on the presence of the trio haplotype, which is strongly linked to the propensity to give birth to multiple calves in one event.

5 Claims, 2 Drawing Sheets

Specification includes a Sequence Listing.

METHODS AND COMPOSITIONS FOR DETERMINING BOVINE OVULATION RATE

CROSS-REFERENCE TO RELATED APPLICATIONS

This application claims the benefit of U.S. Provisional Patent Application Ser. No. 61/841,723, filed Jul. 1, 2013, which is incorporated herein as if set forth in its entirety.

STATEMENT REGARDING FEDERALLY SPONSORED RESEARCH

This invention was made with government support under 12-CRHF-0-6055 awarded by the USDA/NIFA. The government has certain rights in the invention.

BACKGROUND

Commercial cattle breeding constantly strives for ways to increase the efficiency of its operations. One relevant issue for this sector is the frequency with which multiple calves are born in one event (known as the "twinning" rate), which is of concern to both dairy and beef cattle breeding. Twinning, albeit, a relatively low frequency event, is disadvantageous in the production of dairy cattle, since cows having multiple births generally produce lower quantities of milk, and for shorter periods of time than cows having single births. On the other hand, multiple births in beef cattle can be desirable due to the additional calves per birth. Twinning has a heritable, multigenic basis, but the specific genes underlying twinning have not yet been identified. Thus, there is an ongoing need to understand and exploit the genetic basis of twinning for selective cattle breeding so as to decrease or increase twinning rates depending on the particular cattle breeding sector, e.g., dairy cattle or beef cattle.

BRIEF SUMMARY OF THE INVENTION

The invention relates generally to methods and compositions for modulating bovine "twinning rate" based on selective breeding according to the presence or absence of the "trio" haplotype.

Accordingly, in one aspect presented herein is a method for increasing beef cattle production, comprising: breeding a bull or cow identified as trio+; whereby (i) the bred cow has an increased likelihood, relative to a cow of unknown trio haplotype status, of giving birth to multiple calves in one event; and (ii) trio+ female progeny of the bred bull or cow have an increased likelihood, relative to a cow of unknown trio haplotype status, of giving birth to multiple calves in one event.

In some embodiments of the first aspect, the method includes genotyping the bull or cow for the presence or absence of the trio haplotype prior to step (i) of the method. In some embodiments, the method also includes a step of obtaining a biological sample from the bull or cow to be bred, where the biological sample contains an autologous genomic DNA from the bull or cow to be bred.

In some embodiments, breeding the bull or cow includes an artificial insemination step.

In a second aspect provided herein is a method for reducing the risk of multiple births in dairy cattle, comprising breeding a trio− bull or cow identified as trio−; whereby (i) the cow has a decreased likelihood, relative to a cow of unknown trio haplotype status, of giving birth to multiple calves in one event; and (ii) trio− female progeny of the bred bull or cow have a decreased likelihood, relative to a cow of unknown trio haplotype status, of giving birth to multiple calves in one event.

In some embodiments, the method also includes a step of obtaining a biological sample from the bull or cow to be bred, where the biological sample contains an autologous genomic DNA from the bull or cow to be bred (e.g., genomic DNA). In some embodiments, breeding the bull or cow includes an artificial insemination step.

In a third aspect described herein is a method for selective beef cattle breeding, comprising: (i) genotyping a bull or cow for the presence or absence of the trio haplotype; and (ii) breeding the genotyped bull or cow if and only if the genotyped bull or cow is trio+.

In a fourth aspect described herein is a method for selective dairy cattle breeding, comprising: (i) genotyping a bull or cow for the presence or absence of the trio haplotype; and (ii) breeding the genotyped bull or cow if and only if the genotyped bull or cow is trio−.

In a fifth aspect provided herein is a method for determining the likelihood of a cow giving birth to multiple calves in one event, comprising:
  (i) genotyping a cow for the presence or absence of the trio haplotype;
  (ii) indicating that the genotyped cow has a high likelihood of giving birth to multiple calves in one event if and only if the genotyped cow is trio+.

In some embodiments of the fifth aspect, the method also includes the step of breeding the genotyped cow if the genotyped cow is trio+.

In other embodiments, the method also includes marking the genotyped cow to indicate the presence or absence of the trio haplotype.

In a sixth aspect provided herein is a method for determining the likelihood that breeding a cow or bull will yield female offspring likely to give birth to multiple calves in one event, comprising: (i) genotyping a cow or bull for the presence or absence of the trio haplotype; and (ii) indicating the female offspring of the genotyped cow or genotyped bull have a high likelihood, relative to cows of unknown trio haplotype status, of yielding female offspring giving birth to multiple calves in one event, if and only if, the genotyped cow or genotyped bull is trio+.

In some embodiments of the sixth aspect, the method also includes breeding the genotyped cow or bull if the genotyped cow or genotyped bull is trio+.

In some embodiments of the sixth aspect, the method also includes marking the genotyped bull or cow to indicate the presence or absence of the trio haplotype.

In some embodiments of the sixth aspect, the method also includes sorting the genotyped cow or bull into herds based on the presence or absence of the trio haplotype.

In a seventh aspect disclosed herein is a kit for identifying the presence of the trio haplotype in a bovine biological sample, where the kit includes at least two of: (i) a primer set to detect a first polymorphism comprising a 4 base pair indel at base pair 13,663,941 of BTA10; (ii) a primer set to detect a second polymorphism comprising a C to A transversion at base pair 14,263,362 of BTA10; and (iii) a primer set to detect a third polymorphism comprising an A to G transition at base pair 14,270,483 of BTA10.

In some embodiments of the seventh aspect the kit comprises a set of oligonucleotides corresponding to SEQ ID NOs:1-10 along with instructions for their use.

In an eighth aspect disclosed herein is a beef cattle herd comprising a trio haplotype frequency of 50% or more.

In some embodiments of the eighth aspect the twinning rate of the herd is greater than about 30% (e.g., about 50%).

In a ninth aspect disclosed herein is a dairy cattle herd comprising a trio haplotype frequency of less than 3%. In some embodiments, the twinning rate is lower than 1%.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein.

Figure 1:
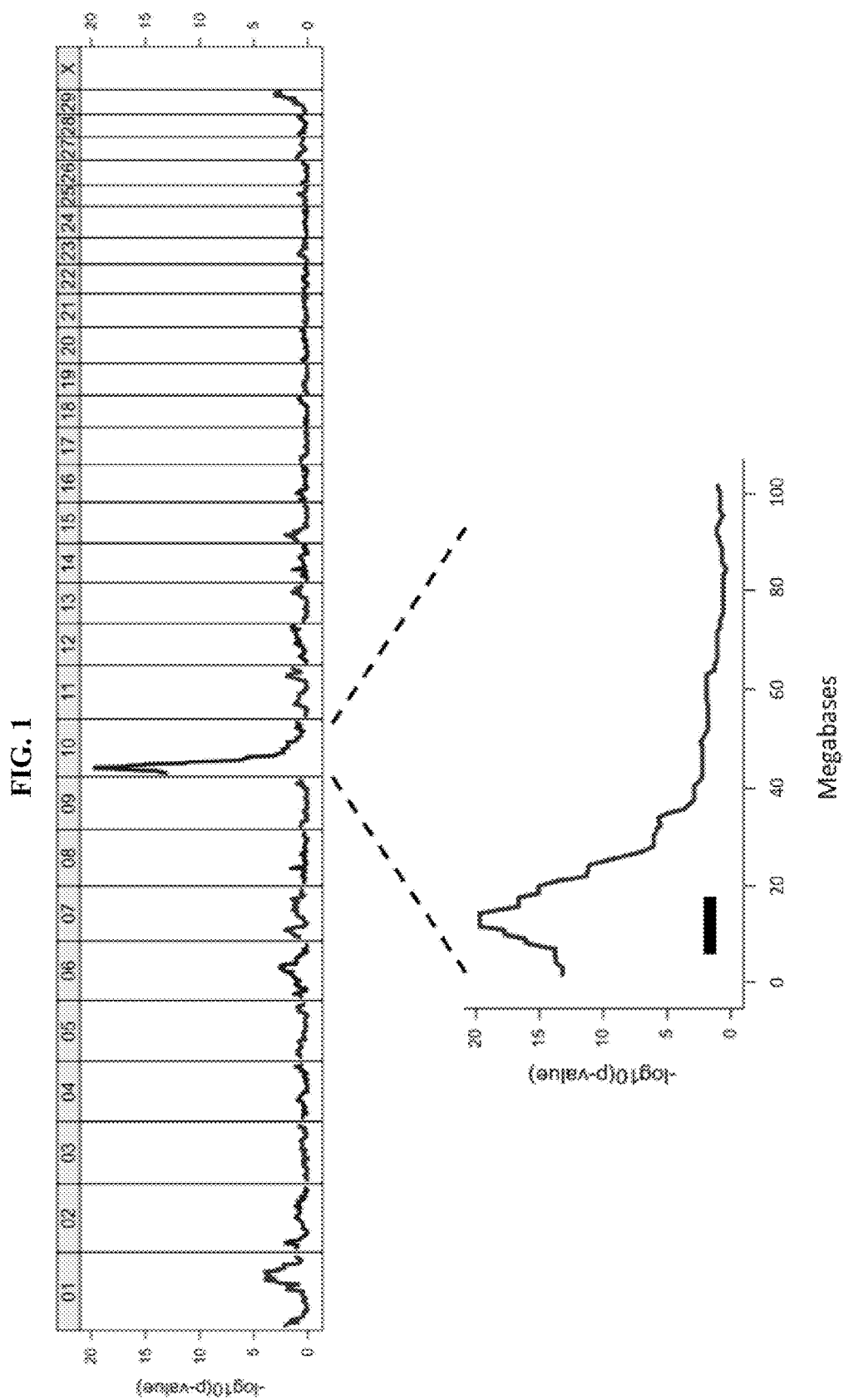
FIG. 1 shows the results of genome-wide, within family linkage analysis for ovulation rate using a 3K bovine SNP chip. The y-axis denotes the $-\log_{10}$ of the nominal p-value from the regression of ovulation rate on paternally inherited haplotype (coded as 0 or 1 for alternative sire haplotypes for an interval bracketed by adjacent SNPs). The x-axis denotes SNP locations in megabases with vertical panels in the upper figure denoting specific chromosomes. A major gene for ovulation rate was mapped to chromosome 10 with a nominal $p<1\times10^{-19}$. The lower figure shows an expanded view of the results for BTA10. The solid rectangle, spanning 10.1 Mb indicates the 95% confidence interval for the gene. Haplotype analysis of individuals recombinant within this interval, using 50 k genotype data, further narrows the genomic location of the gene as illustrated in FIG. 2. The genomic location identified here does not correspond to the locations of any prolificacy genes previously identified or mapped in sheep.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

The present invention is based on the finding that the presence of the trio haplotype is a strong predictor of bovine ovulation and twinning Trio haplotyping is therefore useful for selective breeding in both dairy cattle and meat cattle, as described in further detail below.

I. Definitions

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein.

In describing the embodiments and claiming the invention, the following terminology will be used in accordance with the definitions set out below.

The term "autologous genomic DNA," as used herein refers to genomic DNA of the mammalian organism (e.g., a cow or bull) from which it is derived, as opposed to, e.g., any microbial DNA (e.g., *E. coli*) that may be a contaminant in a biological sample obtained from a mammal.

The term "BTA10," as used herein, refers to bovine chromosome 10.

The term "haplotype," as used herein, refers to a combination of alleles (DNA sequences) at adjacent locations (loci) on a chromosome that are inherited together.

The term "trio haplotype," as used herein refers to the presence in a cow or bull of: a first polymorphism ("polymorphism 1") comprising a 4 base pair insertion or deletion ("indel") at base pair 13,663,941 of BTA10; a second polymorphism ("polymorphism 2") comprising a C to A transversion at base pair 14,263,362 of BTA10; and a third polymorphism ("polymorphism 3") comprising an A to G transition at base pair 14,270,483 of BTA10.

The term "twinning," or "twinning rate" as used herein, refers to a birth of two or more calves, or to the incidence with which twinning occurs in a population, respectively.

II. Methods

Described herein are methods useful for increasing beef cattle production, based on a selective breeding scheme. The methods include breeding a bull or cow previously identified as trio⁺ so as to increase the likelihood relative to a cow of unknown trio haplotype status of giving birth to multiple calves in one event; and (ii) trio⁺ female progeny of the bred bull or cow have an increased likelihood, relative to a cow of unknown trio haplotype status, of giving birth to multiple calves in one event. Typical twinning rates, absent selection of breeding pairs based on trio haplotype status, range from about 1% to about 3.5%.

In some embodiments, such a method includes genotyping a bull or cow for the presence or absence of the trio haplotype, and subsequently selecting the bull or cow for breeding only if they carry the trio haplotype, either as heterozygotes or homozygotes. In some cases, the method also includes obtaining from the bull or cow a biological sample containing an autologous genomic DNA for genotyping. Suitable biological samples for genetic analysis include, but are not limited to, blood, semen, nasal samples, milk, saliva, hair (follicle) samples, and skin punches. In some embodiments, breeding is carried out by artificial insemination.

The methods described herein also enable reducing the risk of multiple births in dairy cattle, which in this case is undesirable since it can lead to reduced milk production. The method includes the steps of breeding a trio-negative (trio⁻) bull or cow that was previously identified as trio⁻; such that (i) the cow has a decreased likelihood, relative to a cow of unknown trio haplotype status, of giving birth to multiple calves in one event; and (ii) trio⁻ female progeny of the bred bull or cow have a decreased likelihood, relative to a cow of unknown trio haplotype status, of giving birth to multiple calves in one event. Optionally, the method can also include genotyping a bull or cow for its trio haplotype status as described above.

Also described herein is a method for selective beef cattle breeding that includes the steps of: (i) genotyping a bull or cow for the presence or absence of the trio haplotype; and (ii) breeding the genotyped bull or cow if and only if the genotyped bull or cow is trio+. Conversely, also described herein is for selective dairy cattle breeding, comprising: (i) genotyping a bull or cow for the presence or absence of the trio haplotype; and (ii) breeding the genotyped bull or cow if and only if the genotyped bull or cow is trio−.

Further described herein is a method for determining the likelihood of a cow giving birth to multiple calves in one event, comprising: (i) genotyping a cow for the presence or absence of the trio haplotype; and (ii) indicating that the genotyped cow has a high likelihood relative to a cow of unknown trio haplotype status, of giving birth to multiple calves in one event if and only if the genotyped cow is trio+. In some embodiments, the just-mentioned method also includes breeding a cow identified as trio+ in the previous steps. In other embodiments, after genotyping the cow, the cow is marked to indicate the presence or absence of the trio haplotype.

Also described herein is a method for determining the likelihood that breeding a cow or bull will yield female offspring likely to give birth to multiple calves in one event, which method includes: (i) genotyping a cow or bull for the presence or absence of the trio haplotype; and (ii) indicating the female offspring of the genotyped cow or genotyped bull have a high likelihood, relative to cows of unknown trio haplotype status, of yielding female offspring giving birth to multiple calves in one event, if and only if, the genotyped cow or genotyped bull is trio+. In some embodiments, the method also includes breeding the genotyped cow or bull if and only if the genotyped cow or bull carry the trio haplotype. In some embodiments, the method also includes marking the genotyped bull or cow to indicate the presence or absence of the trio haplotype.

Methods for isolating genomic DNA of suitable quality for genotyping from a biological sample (e.g., blood) are well known in the art (see e.g., Strauss (2001), Unit 2.2 of *Current Protocols in Molecular Biology*). Suitable methods for determining trio haplotype polymorphisms described herein include, but are not limited to, PCR amplification of Specific Alleles (BI-PASA) assays as described in Liu et al (1997), *Genome Res*, 7(4):389-398; forced PCR-restriction length fragment polymorphism (RFLP) analysis (see, e.g., Rasmussen (2012), "Restriction Fragment Length Polymorphism Analysis of PCR-Amplified Fragments (PCR-RFLP) and Gel Electrophoresis—Valuable Tool for Genotyping and Genetic Fingerprinting," *Gel Electrophoresis—Principles and Basics*, Dr. Sameh Magdeldin (Ed.). In one embodiment, a genomic DNA to be genotyped for the presence or absence of the trio haplotype is assayed for polymorphism 1 using a BI-PASA assay, and polymorphisms 1 and 2 are assayed by forced PCR-RFLP analysis. Such assays are used to determine not only the presence or absence of these polymorphisms, but also whether the polymorphism, when present, is carried as a heterozygous or homozygous allele.

Where cattle are to be marked to indicate a trio haplotype status (i.e., positive or negative), cattle can be marked by any of a number of methods including, but not limited to, ear notching, ear tags, tattooing, freeze branding, hot iron branding, and an electronic markers (e.g., an RFID tag).

III. Compositions

Also described herein is a kit for identifying the presence of the trio haplotype in a bovine biological sample, where the kit includes: (i) a primer set to detect a first polymorphism comprising a 4 base pair indel at base pair 13,663,941 of BTA10; (ii) a primer set to detect a second polymorphism comprising a C to A transversion at base pair 14,263,362 of BTA10; and (iii) a primer set to detect a third polymorphism comprising an A to G transition at base pair 14,270,483 of BTA10. In one embodiment, the kit comprises a set of oligonucleotides corresponding to SEQ ID NOs:1-10 along with instructions for their use as described below. The primers for the 13,663,941 polymorphism (Bi-PASA assay) are as follow:

```
P primer (SEQ ID NO: 1):
TCACTGCTGCACAACCTTTTCTCT

Q primer (SEQ ID NO: 2):
TGGATGCTCATGACTGGATGTTGA

A Primer (SEQ ID NO: 3):
ggggcgggcgAGTTGCGCAGTATGTATG

B Primer (SEQ ID NO: 4):
ggggcgggcGGCAACTAAGCTCATACTG

PQ product: 585 bp

AQ product: 427 bp (for the "+"
allele)

BP product: 194 bp ("-" allele)
```

The primers for the 13,663,941 polymorphism (PCR-RFLP assay) are as follow:

```
SEQ ID NO: 5:
tttgCTCAGTAGTTGCGCAGTACG

SEQ ID NO: 6:
AAATTGAGTTGGGGGCTTCC

PCR product length is 141 bp

PCR product digested with either SnaBI or
HpyCH4IV restriction enzymes:
"+" allele - 23 bp and 122 bp "-" allele - 141 bp
```

The primers for the 14,263,362 polymorphism (PCR-RFLP assay) are as follow:

```
SEQ ID NO: 7:
GGGTCGTGTATCGCACTTTGTT

SEQ ID NO: 8:
TTGTCCCTCTTCCCACAGGTAA

PCR product length: 307 bp

PCR product digested with HpyCH4III
A allele - digested fragment is 307 bp

C allele - digested fragments are 188 bp
and 119 bp
```

The primers for 14,270,483 polymorphism (PCR-RFLP assay) are as follow:

```
SEQ ID NO: 9:
gTTTGCTCCCAAGAAAGACAAGAACAT

SEQ ID NO: 10:
ATGGAGCTTGGCACACAACC

PCR product length: 128 bp

PCR product digested with NlaIII:
A allele - 128 bp

G allele - 26 bp and 102 bp
```

One of ordinary skill in the art will appreciate that suitable primers for such a kit will vary in length depending on the GC composition of the sequence, the desired Tm, the position of the polymorphism within the target sequence, and the particular genotyping method to be used as described herein.

Also described herein is a beef cattle herd that has a trio haplotype frequency of 30% or more, where the beef cattle herd has a twinning rate that is higher than a naturally occurring beef cattle herd having a lower trio haplotype frequency. In some embodiments, such a beef cattle herd has a twinning rate greater than about 50%, e.g., about, 60%, 65%, 70%, 80%, 85%, 90%, or another twinning rate greater than about 50%. In other embodiments, the twinning rate in the herd is greater than about 50%.

Further provided herein is a dairy cattle herd comprising a trio haplotype frequency of less than 3% whereby the dairy cattle herd has a twinning rate that is lower than a naturally occurring beef cattle herd having a higher trio haplotype frequency. In some embodiments, the twinning rate is lower than about 3%, e.g., about 2.5%, 2.0%, 1.5%, 1%, 0.8%, 0.7%, 0.5%, 0.3%, 0.07%, 0.03%, 0.01%, 0.008%, 0.005%, 0.003%, 0.001%, or another twinning rate lower than about 3%.

Beef cattle herds with far higher twinning rates, or dairy cattle herds with far lower twinning rates than found naturally are achieved by application of the trio haplotype-based genotyping and selective methods provided herein.

The invention will be more fully understood upon consideration of the following non-limiting Examples.

EXAMPLES

Example 1 Mapping of a Gene Conferring a High Ovulation Rate in Cows

We have mapped a single gene with an allele conferring high ovulation rate (2-5 eggs per cycle vs the typical one) to a narrow region of bovine chromosome 10 (BTA10). The invention consists of a panel of three genetic markers that can be used in combination to track inheritance of the high ovulation rate allele. The high ovulation rate allele has potential applicability to the beef cattle industry for increasing reproductive efficiency with regard to number of offspring produced per cow annually.

Figure 2:
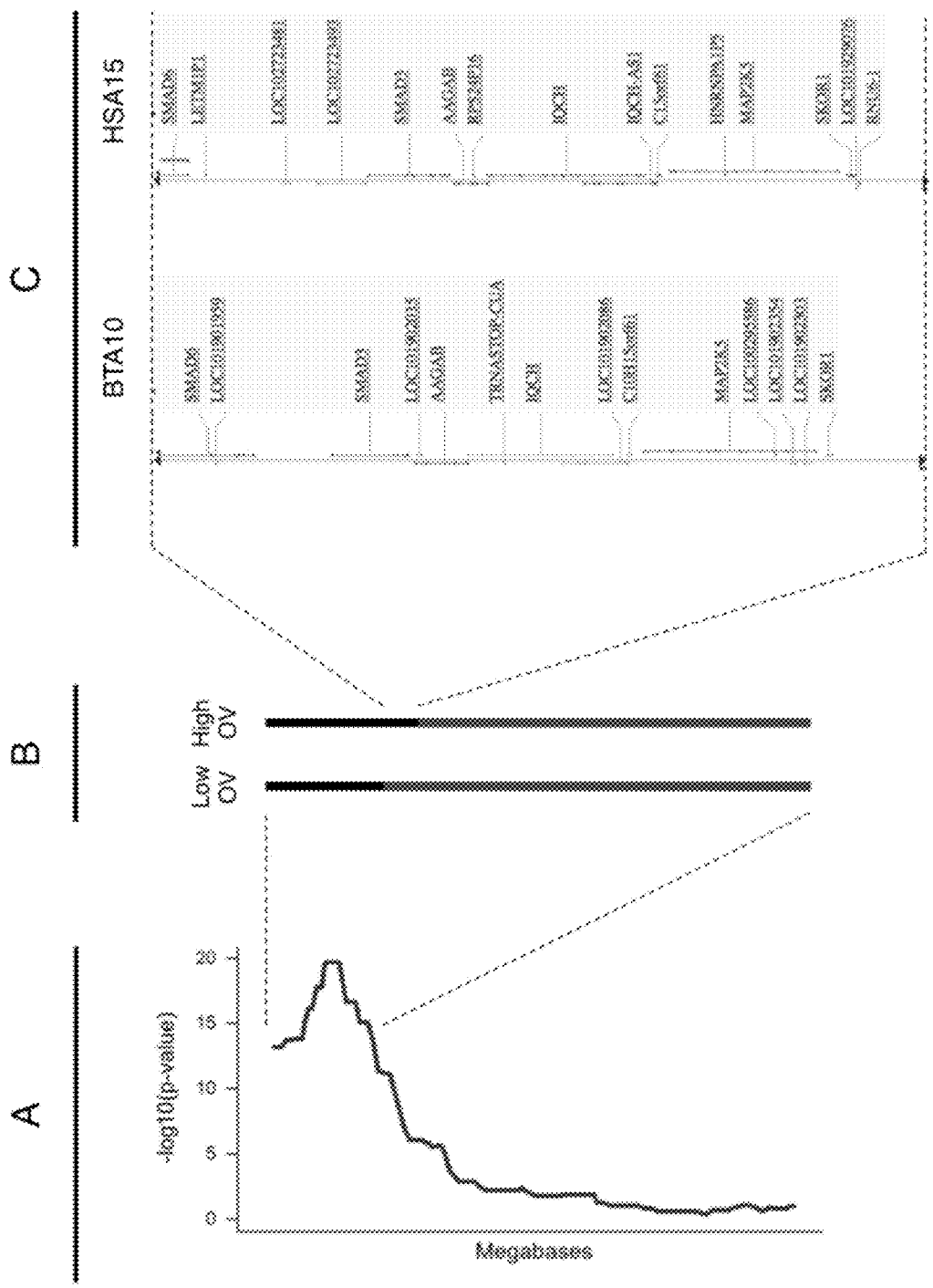
FIG. 2. Positional candidate region on bovine chromosome 10 (BTA10). (A) QTL plot from FIG. 1, re-oriented vertically so that centromeric end is at top. Trio and daughters recombinant within the peak of the QTL plot were genotyped with the Illumina Bovine 50 k BeadChip for fine mapping. (B) Haplotypes of the two recombinant daughters whose recombination events most narrowly bound the gene location (paternally inherited chromosomes depicted within a 20 Mb region spanning the peak of the QTL plot, high ovulation haplotype in black and low ovulation haplotype in grey). Analysis of 50 k SNP data for SNPs informative in this segment resulted in a reduction of the positional candidate gene region to an area of ~2 Mb. Subsequent positional candidate gene analysis identified SNPs in SMAD6 that upon genotyping in the recombinant daughters led to exclusion of SMAD6 and a further narrowing of the positional candidate gene region to a ~1.5 Mb region indicated between the dashed lines in C. Corresponding regions of BTA10 and human chromosome 15 (HSA15) are indicated.

Mapping of the gene has been performed using paternal half-sib daughters of a sire (Trio) that was presumed to be a carrier of the allele for high ovulation rate based on phenotypes of his relatives in a three-generation pedigree. Specifically, Trio's dam produced three sets of triplets during her lifetime (Morris et al. 2010), and Trio produced daughters that had a disproportionately high frequency of twin and triplet births. This information strongly suggested the transmission of a genetic factor between generations. A large (n=116) paternal half-sib family of Trio daughters, produced at the University of Wisconsin-Madison, were evaluated for ovulation rate over an average of four estrous cycles and then genotyped with 3 k SNP chip (containing 2900 SNPs). Linkage analysis was conducted to map the gene to bovine chromosome 10 ($p<10^{-19}$). Genotypic analysis of Trio, daughters recombinant within the likely positional candidate gene region, and select non-recombinant daughters resulted in a narrowing of the positional candidate gene region to an area of ~2 Mb, as shown in FIGS. 1 and 2.

Positional candidate genes, and subsequently the entire 2 Mb region, were examined for SNP and small insertion/deletion (indel) polymorphisms. The positional candidate gene screen failed to reveal a likely causative polymorphism. Likewise, the comprehensive screen of the entire 2 Mb region has as of yet failed to reveal a likely causative polymorphism, though that work is still ongoing. This work did identify 31 validated (true) polymorphisms, and of these, three have the desirable characteristic of having an allele that is associated with the high ovulation rate allele in Trio and uncommon in one or more cattle breeds. When used in combination the rare haplotype associated with Trio's high ovulation rate allele provides the ability to correctly predict inheritance of the high ovulation rate allele greater than 96% of the time. The specific details regarding the polymorphisms are as follows:

Polymorphism 1 is a 4 bp indel at bp 13,663,941 of BTA10,

Polymorphism 2 is a C>A transversion at bp 14,263,362 of BTA10, and

Polymorphism 3 is a A>G transition at bp 14,270,483 of BTA10.

We have used either a Bi-PASA assay (Liu et al. 1997) or a forced PCR-RFLP assay to detect polymorphism 1 and forced PCR-RFLP to detect polymorphisms 2 and 3, though a multitude of different assay types could be designed to detect each of the three.

Example 2

As a confirmation of the tight correlation between the trio haplotype and high ovulation and twinning rates, we analyzed haplotype, ovulation, and birth records of a UW breeding herd. We found that 66 heifers with the trio$^+$ haplotype had an average ovulation rate of 2.19 ova per cycle versus 1.14 ova per cycle for 64 heifers with the trio$^-$ haplotype Six females used in the UW breeding herd prior to this year had the following cumulative records: three females with the trio$^+$ haplotype had one triplet set, two twin sets and two singles. Three females with the trio$^-$ haplotype had four single births.

These results were consistent with the expected predictive value of trio haplotype with respect to ovulation and twinning rates.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

REFERENCES

Morris, C. A., M. Wheeler, G. L. Levet, and B. W. Kirkpatrick. 2010. A cattle family in New Zealand with triplet calving ability. Livestock Science 128:193-196. Liu, Q., E. C. Thorland, J. A. Heit and S. S. Sommer. 1997. Overlapping PCR for bidirectional PCR amplification of specific alleles: a rapid one-tube method for simultaneously differentiating homozygotes and heterozygotes.

What is claimed is:

1. A method for increasing beef cattle production, comprising:
   (a) obtaining a biological sample from a bull or cow to be bred;
   (b) genotyping a bull or cow for the presence or absence of a trio haplotype (trio$^+$) using a panel of genetic markers consisting of:
      (i) a first polymorphism comprising a 4 base pair insertion or deletion at base pair 13,683,941 of bovine chromosome 10 (BTA10);
      (ii) a second polymorphism comprising a C to A transversion at base pair 14,263,362 of BTA10; and
      (iii) a third polymorphism comprising an A to G transition at base pair 14,270,483 of BTA10;
   wherein the presence of the first, second and third polymorphisms identifies the bull or cow as trio$^+$; and
   (c) selectively breeding the bull or cow identified as trio$^+$;
   wherein a bred trio$^+$ cow has an increased likelihood, relative, to a cow of unknown trio$^+$ haplotype status, of giving birth to multiple calves in one pregnancy: and a trio$^+$ female progeny of a bred trio$^+$ bull or bred trio$^+$ cow has an increased likelihood, relative to a cow of unknown trio haplotype status, of giving birth to multiple calves in one pregnancy, whereby multiple calve births provide an increase in beef cattle production.

2. The method of claim 1, wherein the biological sample comprises an autologous genomic DNA sample of the bull or cow to be bred.

3. The method of claim 1, wherein the breeding comprises an artificial insemination step.

4. The method of claim 1, wherein the first, second and third polymorphisms are identified by genotyping assays independently-selected from: Polymerase Chain Reaction Amplification of a Specific Allele (PASA); and Restriction Fragment Length Polymorphism Analysis of a Polymerase Chain Reaction-Amplified Fragment (PCR-RFLP).

5. The method of claim 4, wherein: (a) the first polymorphism is identified by PASA assay using a primer set comprising the oligonucleotides set forth in SEQ ID NO:1, SEQ ID NO:2, SEQ ID NO:3, and SEQ ID NO:4, or PCR-RFLP assay using a primer set comprising the oligonucleotides set forth in SEQ ID NO:5 and 6; (b) the second polymorphism is identified by PCR-RFLP assay using a primer set comprising the oligonucleotides set forth in SEQ ID NO:7 and 8; and (c) the third polymorphism is identified b PCR-RFLP assay using a primer set comprising the oligonucleotides set forth in SEQ ID NO: 9 and 10.

* * * * *

UNITED STATES PATENT AND TRADEMARK OFFICE
CERTIFICATE OF CORRECTION

PATENT NO. : 10,098,332 B2
APPLICATION NO. : 14/321036
DATED : October 16, 2018
INVENTOR(S) : Brian Wayne Kirkpatrick Page 1 of 1

It is certified that error appears in the above-identified patent and that said Letters Patent is hereby corrected as shown below:

In the Claims

Claim 1 (i), Column 11, Line 48, Replace "13,683,941" with --13,663,941--

Signed and Sealed this
Eighteenth Day of May, 2021

Drew Hirshfeld
*Performing the Functions and Duties of the
Under Secretary of Commerce for Intellectual Property and
Director of the United States Patent and Trademark Office*

SEQUENCE LISTING

<160> NUMBER OF SEQ ID NOS: 10

<210> SEQ ID NO 1
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 1
tcactgctgc acaaccttttt ctct                     24

<210> SEQ ID NO 2
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 2
tggatgctca tgactggatg ttga                     24

<210> SEQ ID NO 3
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 3
ggggcgggcg agttgcgcag tatgtatg                 28

<210> SEQ ID NO 4
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 4
ggggcgggcg gcaactaagc tcatactg                 28

<210> SEQ ID NO 5
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 5
tttgctcagt agttgcgcag tacg                     24

<210> SEQ ID NO 6
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 6
aaattgagtt gggggcttcc                          20

<210> SEQ ID NO 7
<211> LENGTH: 22
<212> TYPE: DNA
<213> ORGANISM: Artificial Sequence

```
<220> FEATURE:
<223> OTHER INFORMATION: oligonucleotide primer

<400> SEQUENCE: 7
gggtcgtgta tcgcactttg tt                                            22

<210> SEQ ID NO 8
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 8
ttgtccctct tcccacaggt aa                                            22

<210> SEQ ID NO 9
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 9
gtttgctccc aagaaagaca agaacat                                       27

<210> SEQ ID NO 10
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 10
atggagcttg gcacacaacc                                               20
```